United States Patent [19]

Franz et al.

[11] 3,954,598

[45] May 4, 1976

[54] PURIFICATION OF AQUEOUS UREA SOLUTIONS IN A UREA DEWAXING PROCESS

[75] Inventors: Hermann Franz, Neu Isenburg; Max Kunert, Neu Wulmstorf, both of Germany

[73] Assignee: Edeleanu Gesellschaft m.b.H., Germany

[22] Filed: Apr. 28, 1975

[21] Appl. No.: 572,685

Related U.S. Application Data

[63] Continuation of Ser. No. 218,515, Jan. 17, 1972, abandoned, which is a continuation-in-part of Ser. No. 29,253, April 16, 1970, abandoned.

[30] Foreign Application Priority Data

Apr. 18, 1969  Germany.............................. 1919663

[52] U.S. Cl.............................. 208/25; 260/96.5 C
[51] Int. Cl.$^2$.................... C07B 21/00; C10G 43/04
[58] Field of Search.................. 208/25; 260/96.5 R, 260/96.5 C

[56] References Cited
UNITED STATES PATENTS

| 3,269,935 | 8/1966 | Maas et al...................... | 260/96.5 R |
| 3,661,766 | 5/1972 | Franz et al..................... | 260/96.5 R |

*Primary Examiner*—Herbert Levine
*Attorney, Agent, or Firm*—T. H. Whaley; C. G. Ries; William E. McNulty

[57] ABSTRACT

Dilute aqueous urea solutions, contaminated with oil-solvent solution and obtained as filtrate or centrifugate in a urea dewaxing process of the type where a concentrated aqueous solution of urea is employed to form the wax-urea adduct, are purified by admixing the contaminated dilute aqueous urea solution with 1–25, preferably 2–5 volumes of solvent per volume of oil-solvent solution contamination, filtering the mixture, settling the mixture into two liquid phases, a substantially uncontaminated aqueous urea solution and an oil-solvent solution, and separating the two phases.

6 Claims, No Drawings

PURIFICATION OF AQUEOUS UREA SOLUTIONS IN A UREA DEWAXING PROCESS

This is a continuation of application Ser. No. 218,515 filed Jan. 17, 1972 which is a continuation-in-part of application Ser. No. 29,253 filed Apr. 16, 1970 now both abandoned.

BACKGROUND OF THE INVENTION

This invention relates to a process for the purification of dilute aqueous urea solutions contaminated with oily substances. It is particularly related to those urea solutions obtained in a urea dewaxing process of the type where a chlorinated hydrocarbon solvent is used as a diluent for the feed and a concentrated aqueous solution of urea is employed to form a urea-wax adduct. More particularly, this process relates to the purification of the aqueous phase portion of the filtrate or centrifugate (hereinafter referred to collectively as filtrate for convenience) resulting from separating the solid adduct from the liquid mixture of oil-solvent solution and aqueous urea solution.

In urea dewaxing processes normal paraffins are separated from hydrocarbon mixtures because of the ability of normal paraffins to pass within the crystalline structure of urea forming a solid adduct. After separating the adduct from the liquid components by filtration or centrifugation, it is decomposed by heat into its components in liquid form for ultimate recovery of the normal paraffins. The several processes which utilize this separation technique may be classified by the physical state of the urea when forming the adduct, to wit: (1) crystalline urea is mixed with the oil containing the normal paraffins, (2) the oil is percolated through a fixed bed of crystalline urea, (3) a dilute urea solution is contacted with the oil, or (4) a concentrated urea solution is contacted with the oil. Processes employing all four techniques are described in Fritz, "Urea Adduct Processes for n-Paraffin Recovery", in "Proceedings of the Symposium on Normal Paraffins" at page 29, European Chemical News Normal Paraffins Supplement, Dec. 2, 1966.

The subject of this invention relates to a urea dewaxing process where a concentrated urea solution is employed for adduct formation. In this dewaxing process, the hydrocarbon mixtures are diluted with oil solvents, preferably chlorinated hydrocarbons such as dichloromethane, and brought into intimate contact with a highly concentrated aqueous solution of urea to form an adduct of urea and n-paraffins. This solid phase adduct is separated from the liquid phases by filtering or centrifuging and then is decomposed at elevated temperature, often aided by the addition of water, into urea and paraffin. The liquid phases remaining as filtrate are a mixture of hydrocarbons substantially free of normal paraffins and dissolved in the oil solvent - hereinafter called "oily phase" - and an aqueous urea solution. In a settling vessel, known as a separator, the bulk of the aqueous urea solution forms the upper phase while the oily phase is the lower one. Any residual aqueous urea solution is removed from the oily phase by washing with water. The highly dilute aqueous urea solution is combined with the wash water and recycled for use in the adduct decomposition step. Before this is done though, any traces of the oily phase still present in the highly dilute urea solution must be removed. These oily substances would otherwise contaminate the n-paraffins released during the adduct decomposition and considerably affect their quality.

As this urea dewaxing process is presently practiced, metallic filters are often employed to remove the oily phase contamination present in the dilute aqueous urea solutions. As these oily substances are very greasy, they often choke the filter pores sooner than would solid contamination. Moreover, it is practically impossible to clean the filters by back flushing, so that new filters have to be inserted continually. In that respect, this filtering problem is different from known filtering problems.

It is therefore an objective of the invention to remove the oily phase contamination from the dilute aqueous urea filtrate in such a way that the filter pores are not so quickly clogged as heretofore. Another objective of the invention is to modify the contamination so that the clogged filters can be rapidly reactivated by back flushing with water. Furthermore, the invention is aimed at solving the said problems in such a manner that no additional materials are required than those which are normally used in the prior art urea dewaxing process wherein the adduct is formed from a concentrated aqueous urea solution.

SUMMARY OF THE INVENTION

The oily phase contamination present in the dilute aqueous urea solution which constitutes one of the phases present in the filtrate remaining after the urea-normal paraffin adduct is separated from the liquid in a urea dewaxing process, is substantially removed by admixing quantities of chlorinated hydrocarbon solvent with the contaminated dilute aqueous urea solution, filtering the resultant mixture, allowing the filtered mixture to settle and separating the several phases produced.

DESCRIPTION OF THE PREFERRED EMBODIMENTS

In accordance with the present invention which relates to a urea dewaxing process wherein a concentrated aqueous urea solution is contacted with a normal paraffin containing distillate diluted with a chlorinated hydrocarbon solvent to produce the solid adduct, the aqueous portion of the filtrate, passing from the filter employed to remove the adduct and containing a minor but undesirable quantity of the oily phase portion of the filtrate, is purified by admixing a quantity of the distillate solvent, usually a chlorinated hydrocarbon such as dichloromethane, with the contaminated dilute aqueous urea solution, filtering with mixture, allowing it to settle and separating the resultant phases. For this purpose, the oil solvent used is a chlorinated hydrocarbon and is the one which serves as the diluent for the hydrocarbon mixture feed from which the n-paraffins are to be removed. Dichloromethane is the preferred solvent. Of course, a mixture of chlorinated hydrocarbons may be used as well. The volume of the oil solvent required is determined by the quantity of the oily substances to be removed and should be between 1 and 25 times the estimated volume of the oily phase contamination. To avoid excessive use of solvent, preferably a volume of solvent two to five times the volume of oily phase contamination is used.

Admixing may be done by introducing the dilute urea solution to be purified and the oil solvent into a common pipe or by feeding them together into a pump which discharges the mixture through the filter. Filters preferred for use employ filter cartridges containing, for example, porous clay or sintered metal balls. The contamination deposited in the filter pores during filtration can now easily be removed by back flushing with water.

The filtered liquid quickly separates into two layers. The lower layer contains the chlorinated hydrocarbon solvent with the oily phase substances diluted therein. This layer is treated by known methods, for example, by distillation. However, it may advantageously be used for diluting the hydrocarbon feed mixtures from which n-paraffins are to be removed. If recovered by distillation the chlorinated hydrocarbon is used, depending on the yield and the process requirements, for diluting the hydrocarbon feed mixtures and/or purifying, according to this invention, the dilute aqueous urea solution.

The upper layer is the purified dilute aqueous urea solution, which may now be used for adduct decomposition.

The following example serves to illustrate the invention without limiting the scope thereof:

A hydrocarbon mixture containing normal paraffins is admixed with dichloromethane and then contacted with a concentrated aqueous urea solution to form an adduct of urea and normal paraffins. The solid adduct is removed by filtration leaving a filtrate which upon settling in a separator forms two phases - an aqueous urea phase and an oily phase comprising hydrocarbons and dichloromethane. The aqueous urea phase contains a small quantity of the oily phase. 500 liters per hour of the dilute aqueous urea solution having an oil phase contamination content of 3,700 mg/l are removed from the separator through a ½ inch pipe. 50 liters of dichloromethane are injected through a tee into this liquid stream. After filtration through a porous metal ball filter having a pore size of $10^{-3}$ mm, two layers settle quickly. The lower dichloromethane layer contains most of the oily phase contamination, while the upper layer contains the aqueous urea solution having an oily phase content of only about 50 mg/l. The volume of dichloromethane used to purify the aqueous urea solution is about 23 times the volume of the oily phase contamination since the density ($d_{15}$) of the contamination is about 0.85 g/ml., amounting to about 2.18 liters/hour.

We claim:

1. A process for the purification of an aqueous solution contaminated with a quantity of an oily phase comprising a mixture of hydrocarbons and dichloromethane, said solution obtained as a portion of the aqueous phase of the filtrate following removal of a solid adduct of urea and normal paraffins in a urea dewaxing process of the type utilizing a concentrated aqueous urea solution to form the adduct, which comprises:
   a. admixing an effective amount, sufficient to substantially remove the oily phase contamination, of dichloromethane with the aqueous urea solution containing the oily phase contamination,
   b. filtering the resultant mixture,
   c. allowing the mixture to settle forming two layers,
   d. separating the layers to yield a lower layer comprising dichloromethane and a quantity of the oily phase contamination and an upper layer comprising aqueous urea solution having a substantially reduced oil phase contamination content.

2. A process according to claim 1 wherein the volume of dichloromethane in step (a) is about 23 times the volume of oily phase contamination.

3. A process according to claim 2 wherein the volume of dichloromethane is 2 to 5 times the volume of oily phase contamination.

4. In a urea dewaxing process wherein a hydrocarbon mixture containing normal paraffins is admixed with a chlorinated hydrocarbon solvent producing an oil-solvent mixture and wherein said oil-solvent mixture is contacted with a concentrated aqueous urea solution forming a solid adduct of normal paraffin and urea and wherein said adduct is separated from the liquid mixture and wherein the liquid mixture separates into an oil phase comprising oil and solvent and an aqueous phase comprising aqueous urea solution contaminated with a quantity of the oily phase, the improvement which comprises:
   a. admixing an effective amount, sufficient to substantially remove the oily phase contamination, of a chlorinated hydrocarbon solvent with the aqueous phase, said chlorinated hydrocarbon solvent being the same chlorinated hydrocarbon solvent admixed with the hydrocarbon mixture prior to adduct formation,
   b. filtering the resultant mixture,
   c. settling the mixture forming two layers,
   d. separating the layers to yield a lower layer comprising chlorinated hydrocarbon solvent and a quantity of the oily phase contamination and an upper layer comprising aqueous urea solution having a substantially reduced oily phase contamination content.

5. A process according to claim 4 wherein the chlorinated hydrocarbon solvent is dichloromethane and the volume of the chlorinated hydrocarbon solvent in step (a) is about 23 times the volume of oily phase contamination.

6. A process according to claim 5 wherein the volume of the chlorinated hydrocarbon solvent is 2 to 5 times the volume of oily phase contamination.

* * * * *